United States Patent
Tani et al.

(10) Patent No.: US 7,450,684 B2
(45) Date of Patent: Nov. 11, 2008

(54) GLASS RECOVERY METHOD

(75) Inventors: Yoshiyuki Tani, Osaka (JP); Takao Hisazumi, Osaka (JP)

(73) Assignee: Panasonic Corporation, Osaka (JP)

(*) Notice: Subject to any disclaimer, the term of this patent is extended or adjusted under 35 U.S.C. 154(b) by 24 days.

(21) Appl. No.: 10/593,822

(22) PCT Filed: May 23, 2005

(86) PCT No.: PCT/JP2005/009349

§ 371 (c)(1),
(2), (4) Date: Sep. 22, 2006

(87) PCT Pub. No.: WO2005/116618

PCT Pub. Date: Dec. 8, 2005

(65) Prior Publication Data

US 2007/0189435 A1    Aug. 16, 2007

(30) Foreign Application Priority Data

May 27, 2004   (JP)   ................ 2004-157385

(51) Int. Cl.
G01N 23/223    (2006.01)
(52) U.S. Cl. .......................... 378/45; 378/53
(58) Field of Classification Search ............ 378/45, 378/53
See application file for complete search history.

(56) References Cited

U.S. PATENT DOCUMENTS

| | | | | | |
|---|---|---|---|---|---|
| 3,802,558 | A | * | 4/1974 | Rhys | ................ 209/557 |
| 3,980,180 | A | * | 9/1976 | Jamieson | ............ 209/565 |
| 5,663,997 | A | * | 9/1997 | Willis et al. | ............ 378/45 |
| 5,718,737 | A | * | 2/1998 | Mosch | ............ 65/30.1 |
| 6,129,779 | A | * | 10/2000 | Bohland et al. | ........ 75/714 |
| 6,230,521 | B1 | * | 5/2001 | Lehman | ............ 65/29.11 |
| 6,888,917 | B2 | * | 5/2005 | Sommer | ............ 378/58 |
| 2003/0147494 | A1 | | 8/2003 | Sommer, Jr. et al. | |

FOREIGN PATENT DOCUMENTS

| | | |
|---|---|---|
| DE | 195 26 212 A1 | 1/1997 |
| JP | 55-70873 A | 5/1980 |
| JP | 02-273439 | 11/1990 |

(Continued)

OTHER PUBLICATIONS

Yasuhiro Suzuki, et al., "Hoshako Keiko X-sen Bunsekiho Oyobi Yudo Ketsugo Plasma Shitsuryo Bunsekiho ni yoru Head light Glass Chu Biryo Fujunbutsu no Bunseki to Hokagakuteki ido Shikibetsu heno Oyo," Jun. 5, 2003, pp. 469-474, vol. 52, No. 6.

Akiki Hokura et al., "Kahangata X-sen Bunseki Sochi ni yoru Shutsudo Ibutsu no Sonoba Bunseki," Dai 6 Kai Bunseki Kagaku Tokyo Symposium 2002 Kiki Bunseki Tokyo Toronkai Koen Yoshishu, Sep. 4, 2002, p. 82.

Yasuhiro Suzuki et al., "Forensic Discrimination of Headlignt Glass by Analysis of Trace Impurities With Synchrontron Radiation X-Ray Fluorescence Spectrometry and ICP-MS"(English abstract).

(Continued)

Primary Examiner—Chih-Cheng G Kao
Assistant Examiner—Thomas R Artman
(74) Attorney, Agent, or Firm—McDermott Will & Emery LLP

(57) ABSTRACT

In a recycling process, the homogeneity of glass cullet decreases and the quality of the recycled glass is diminished. To solve this problem, the present involves using a fluorescent X-ray analyzer to analyze the glass composition of display substrates prior to crushing, and thereby identifying glass of the same composition, converting the same into cullet, and recovering the glass.

17 Claims, 9 Drawing Sheets

FOREIGN PATENT DOCUMENTS

| | | |
|---|---|---|
| JP | 2-273439 A | 11/1990 |
| JP | 4-366526 A | 12/1992 |
| JP | 2503072 | 3/1996 |
| JP | 11-51884 | 2/1999 |
| JP | 11-51884 A | 2/1999 |
| JP | 11-174005 | 7/1999 |
| JP | 11-174005 A | 7/1999 |
| JP | 2002-50294 A | 2/2002 |
| WO | WO 96/23212 | 8/1996 |

OTHER PUBLICATIONS

"Kahangata Keiko X-sen Bunseki Sochi ni yoru Shutsudo ibutsu no Sonoba Bunseki" (English Translation attached).

European Search Report issued in European Patent Application No. EP 05741505.1-1240 PCT/JP2005009349, dated Mar. 5, 2008.

* cited by examiner

GLASS RECOVERY METHOD

RELATED APPLICATIONS

This application is the U.S. National Phase under 35 U.S.C. § 317 of International Application No. PCT/JP2005/009349, filed on May 23, 2005, which in turn claims the benefit of Japanese Application No. 2004-157385, filed on May 27, 2004, the disclosures of which Applications are incorporated by reference herein.

TECHNICAL FIELD

This invention relates to a method and apparatus for identifying glass, and more particularly to identifying the type of glass substrate used for a display.

BACKGROUND ART

As display devices have become larger and thinner in recent years, plasma display panel (hereinafter referred to as PDP) devices, for example, have been under development, and at the same time there has been growing need for this devices to be recycled.

As shown in FIG. 8, a PDP is generally configured such that a front substrate 81 and a rear substrate 82, both made of glass, are sealed together with a sealing material (not shown), and a discharge gas is charged in between the sealed front substrate 81 and rear substrate 82 to form a discharge space. Display electrodes 83, but electrodes 84, a dielectric layer 85, and a protective layer 86 are formed in that order on the front substrate 81. Address electrodes 87 are formed on the rear substrate 82, and these are each coated with a red, green, or blue phosphor 89 via a dielectric layer 88. As shown in the drawing, the red, green, and blue phosphors 89 on the address electrodes 87 are separated from each other by barriers 90 (see, for example, Patent Documents, 1, 2, and 3).

In the past, rejects from manufacturing processes, and electrical products that have been used as products have generally been disposed of by being buried and so forth. In the case of the above-mentioned PDPs, because they contain hazardous substances such as lead in the sealing material or the various layers formed on the front substrate 81 and rear substrate 82, they have to be buried after the hazardous substances have first undergone a solidification treatment. Also, large glass substrates have been used for the front substrate 81 and the rear substrate 82 in order to provide a larger screen. Consequently, the substrates account for greater volume and weight in a product, and recycling is therefore also desirable from the standpoints of cost and the environment. A method for recycling as an industrial material a glass substrate used for the front or rear substrate of a PDP, which has become a reject in the course of manufacture, has been disclosed in the past (see, for example, Patent Document 4).

FIG. 9 shows the conventional procedure in which a recycling procedure S11 is incorporated into a PDP production procedure S10. The details of S10 are not given here, but upon completion of an aging step S95, reject identification is performed in a glass inspection step S96. Any PDP determined here to be defective is sent to S11. S11 comprises mainly a step S98 of separating the front and rear substrates incorporated into a recovered PDP, a step S99 of peeling the layers (surface layers) formed on the separated front and rear substrates, and steps S100 and S101 of separating and recovering the peeled components of the surface layers of the front and rear substrates. Here, in S100, the front and rear substrates are finely crushed into glass cullet (hereinafter referred to as cullet) in order to recycle as glass raw materials the front and rear substrates whose surface layers have been removed.

Patent Document 1: Japanese patent publication No. 2,503,072

Patent Document 2: Japanese published unexamined patent Application No. H4-366526

Patent Document 3: Japanese published unexamined patent Application No. S55-70873

Patent Document 4: Japanese published unexamined patent Application No. 2002-50294

DISCLOSURE OF THE INVENTION

Manufacturers and assemblers of PDPs and other electrical products usually receive their supplies of materials (glass in this case) from a number of different material makers in order to remain competitive in terms of material quality and price. In this case, the compositions of the glass vary from maker to maker. Consequently, when cullet is recovered without first being identified and sorted by maker, the recovered cullet contains glass from a number of different material makers. As a result, this creates a problem in that it lowers the homogeneity of the recovered cullet. Such a cullet can be used in fewer recycling applications, and its value is therefore not as high as it would be otherwise. For instance, when rejects of PDP glass substrates are recycled, the ideal situation would be to recycle the rejects back into PDP glass substrates, but if the homogeneity of the recovered cullet is low, the quality of the glass substrates produced from this material will also decrease. The present invention provides a method for identifying and sorting recovered cullet in order to solve the above problems.

The glass identification method pertaining to the first invention in the present invention glass identification method for recycling a target material that includes glass, comprising, irradiating the target material with X-rays to obtain a fluorescent X-ray spectrum for the target material, and identifying the type of glass included in the target material by analyzing and comparing the fluorescent X-ray spectrum group for a specific substance group with the fluorescent X-ray spectrum of the target material. Identifying the type of glass involves performing compositional analysis of the fluorescent X-ray spectrum of the target material and compositional analysis of the fluorescent X-ray spectrum group of the specific substance group, comparing the analysis results, and determining the degree of agreement.

This increases the homogeneity of the recovered target material and improves recycling precision.

The glass identification method pertaining to the second invention is a glass identification method for recycling a target material that includes glass, comprising, irradiating the target material with X-rays to obtain a fluorescent X-ray spectrum for the target material, identifying the type of glass included in the target material by analyzing and comparing the fluorescent X-ray spectrum group for a specific substance group with the fluorescent X-ray spectrum of the target material. Identifying the type of glass involves finding the difference between the fluorescent X-ray spectrum of the target material and the various spectra of the fluorescent X-ray spectrum group of the specific substance group, and determining the degree of agreement.

This increases the homogeneity of the recovered target material and improves recycling precision.

The glass identification method pertaining to the third invention is the first glass identification method, wherein the target material and/or the specific substance group is a glass substrate used for a display.

This makes it possible to recycle display-use glass substrates.

The glass identification method pertaining to the fourth invention is the first glass identification method, wherein the target material and the specific substance group include at least one element selected from potassium, calcium, iron, strontium, zirconium, barium, and hafnium.

Since display-use glass substrates usually have distinctive contents of the above elements, the type of glass can be identified by analyzing these elements.

The glass identification apparatus pertaining to the fifth invention is a glass identification apparatus comprises an X-ray tube for irradiating a target material that includes a glass with X-rays, a detector for measuring the intensity of fluorescent X-rays emitted from the target material, a memory component for storing data of the fluorescent X-ray spectrum group of the specific substance group, and a computing unit for identifying the type of glass included in the target material by finding the fluorescent X-ray spectrum of the target material from the measurement results of the detector, and analyzing and comparing the fluorescent X-ray spectrum of the target material with the data for the fluorescent X-ray spectrum group of the specific substance group.

This makes it possible to identify the homogeneity of a target material.

With the present invention, the homogeneity of the recovered cullet is increased, which makes it possible to prevent a decrease in the quality of recycled PDP glass, and increases the value of such glass.

The glass identification method pertaining to the sixth invention is the second glass identification method, wherein the target material and/or the specific substance group is a glass substrate used for a display.

This makes it possible to recycle display-use glass substrates.

The glass identification method pertaining to the seventh invention is the second glass identification method, wherein the target material and the specific substance group include at least one element selected from potassium, calcium, iron, strontium, zirconium, barium, and hafnium.

Since display-use glass substrates usually have distinctive contents of the above elements, the type of glass can be identified by analyzing these elements.

Figure 1:
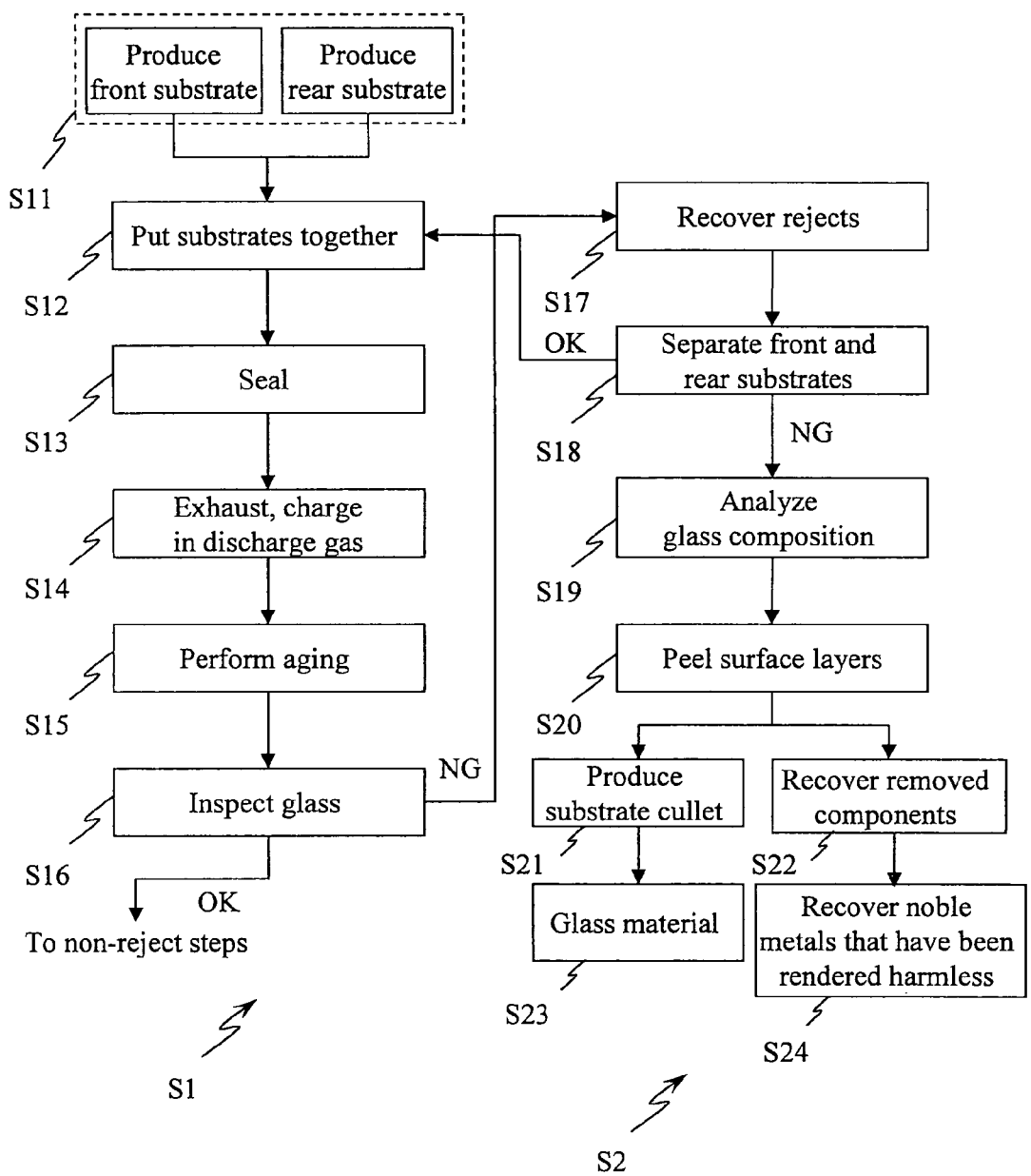
FIG. 1 is a flowchart of the PDP production step and recycling step of the present invention.

NUMERICAL REFERENCES 1 substrate
2 X-ray tube
3 X-rays
4 fluorescent X-rays
5 detector
6 amplifier
7 memory unit
8 computing unit
9 display
10 stage
11 fluorescent X-ray analyzer
81 front substrate
82 rear substrate
83 display electrode
84 bus electrode
85, 88 dielectric layer
86 protective layer
87 address electrode
89 phosphor
90 barrier

DETAILED DESCRIPTION OF THE PREFERRED EMBODIMENT

In this embodiment, the target material will be described as a glass substrate for a PDP.

In the present invention, before the surface layers are removed and the display crushed, the compositions of a recovered PDP glass substrate are analyzed, and just PDP glass of the same compositions is collected and made into cullet, thereby improving the homogeneity of the cullet and allowing it to be recycled as a high-quality PDP glass substrate.

The present invention will now be described in further detail, but is not limited to or by the following descriptions.

Embodiment

FIG. 1 is a flowchart of the PDP production step, including a recycling step, of the present invention. The characteristic feature of the present invention is that the glass components of front and rear substrates deemed to be rejects in a glass inspection step S16 of a PDP production step S1 are identified in a glass composition analysis step S19 of a recycling step S2, and the cullet is accordingly classified.

Figure 2:
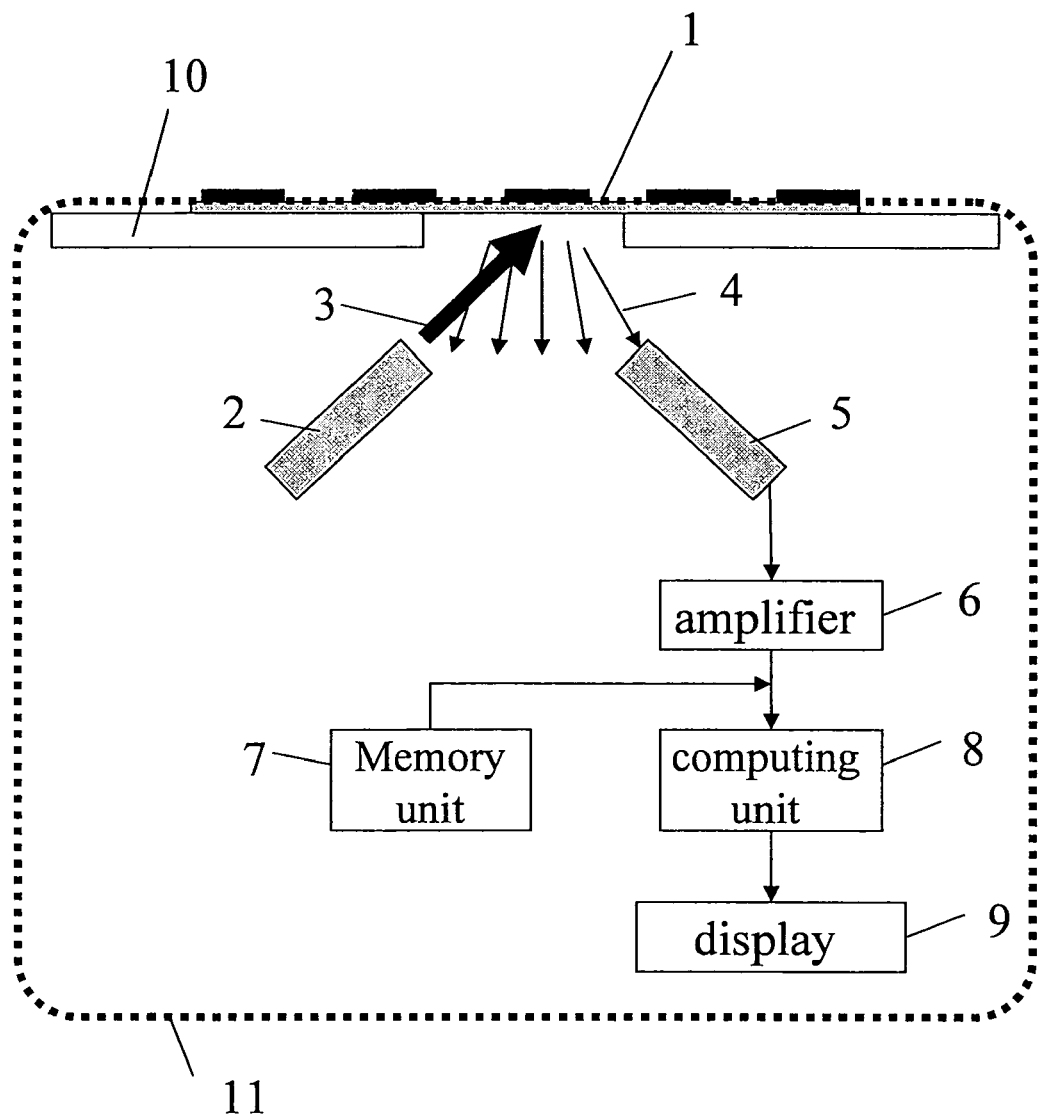
FIG. 2 is a diagram of the structure of the identification apparatus of the present invention.

FIG. 2 is a diagram of the structure of the fluorescent X-ray analyzer 11 (SEA-2210A fluorescent X-ray analyzer made by SII NanoTechnology), which is the glass identification apparatus used to execute this step S19. The reason for using fluorescent X-rays is to keep equipment costs low without damaging the substrate itself during measurement. Also, with a fluorescent X-ray analyzer, compositions can be analyzed on the order of a few tens of parts per million, so performance in terms of precision is satisfactory in the identification of the above-mentioned substrates. Furthermore, the fluorescent X-ray analyzer 11 is an energy-dispersive fluorescent X-ray analyzer. An energy-dispersive fluorescent X-ray analyzer takes advantage of the fact that the energy of fluorescent X-rays is unique to each composition, and measures and analyzes the energy spectrum of fluorescent X-rays to analyze the compositions of a sample, and since the apparatus is inexpensive, it is favorable for the present invention.

In FIG. 2, the fluorescent X-ray analyzer 11 comprises an X-ray tube 2 for irradiating a substrate with specific X-rays 3, a detector 5 for receiving the X-rays 3 and measuring the intensity of fluorescent X-rays 4 emitted from the substrate, an amplifier 6 for amplifying the detection results of the detector 5, and a memory unit 7 for storing data for fluorescent X-ray spectrum groups corresponding to the compositions of a specific plurality of types of PDP substrate. The analyzer further comprises a computing unit 8 for finding the fluorescent X-ray spectrum from the results of the amplifier 6, and comparing analyzing this fluorescent X-ray spectrum with the data stored in the memory unit 7. A display 9 may also be provided for displaying the results of the computing unit 8.

A substrate 1 separated into a front or rear substrate is placed on a stage 10, with the X-ray irradiation side being a side that has not undergone glass processing. When the X-rays 3 emitted by the X-ray tube 2 irradiates the substrate 1, the substrate 1 emits fluorescent X-rays 4, and these fluorescent X-rays 4 are detected by the detector 5. The detected X-ray dose is amplified by the amplifier 6, and measured as the fluorescent X-ray spectrum by the computing unit 8.

Examples and the results thereof will now be given.

EXAMPLE 1

In this example, composition analysis is used as a PDP glass identification standard.

PDP glass that was deemed to be a reject from the production process was used as a sample material, which was subjected to a composition analysis experiments by fluorescent X-ray analysis. The results are given in Table 1. The amounts in which the compositions are contained are given as weight percentages (wt %).

TABLE 1

| | Composition content (wt %) Sample material |
|---|---|
| $Al_2O_3$ | 10.282 |
| $SiO_2$ | 66.533 |
| $K_2O$ | 5.498 |
| CaO | 3.780 |
| $Fe_2O_3$ | 0.108 |
| SrO | 5.137 |
| $ZrO_2$ | 1.926 |
| BaO | 6.653 |
| $HfO_2$ | 0.084 |

Next, PDP glass was procured from two glass manufacturers that supply substrates (hereinafter referred to as Company A and Company B), and these were used as reference samples which were subjected to fluorescent X-ray analysis just as in the case of Table 1. The results are given in Table 2. The reference samples are termed sample 1 (made by Company A) and sample 2 (made by Company B).

TABLE 2

| | Composition content (wt %) | |
|---|---|---|
| | Sample 1 | Sample 2 |
| $Al_2O_3$ | 10.282 | 10.562 |
| $SiO_2$ | 66.533 | 70.279 |
| $K_2O$ | 5.498 | 5.452 |
| CaO | 3.780 | 1.720 |
| $Fe_2O_3$ | 0.108 | 0.076 |
| SrO | 5.137 | 4.806 |
| $ZrO_2$ | 1.926 | 2.145 |
| BaO | 6.653 | 4.905 |
| $HfO_2$ | 0.084 | 0.055 |

A comparison of the results in Tables 1 and 2 reveals that the compositions of the sample material in this material match the compositions of reference sample 1. This tells us that the recovered PDP glass is a sample 1, that is, glass made by Company A.

With the above method, approximately 100 kg of substrate identified as sample 1 was recovered and redissolved, and the material was checked to see if it could be recycled as PDP glass. As a result, it was confirmed that it could be satisfactorily recycled as PDP glass without having to add any new steps to the production step S11.

EXAMPLE 2

In this example, the spectra of various samples obtained by fluorescent X-ray analysis were used as PDP glass identification standards. More specifically, in the glass composition analysis step S19, the difference in the spectra between the sample material and the reference samples was found by the computing unit 8, and this was used to determine the homogeneity of the sample material. The sample material, the reference samples, and the identification apparatus were the same as in Example 1.

Figure 3:
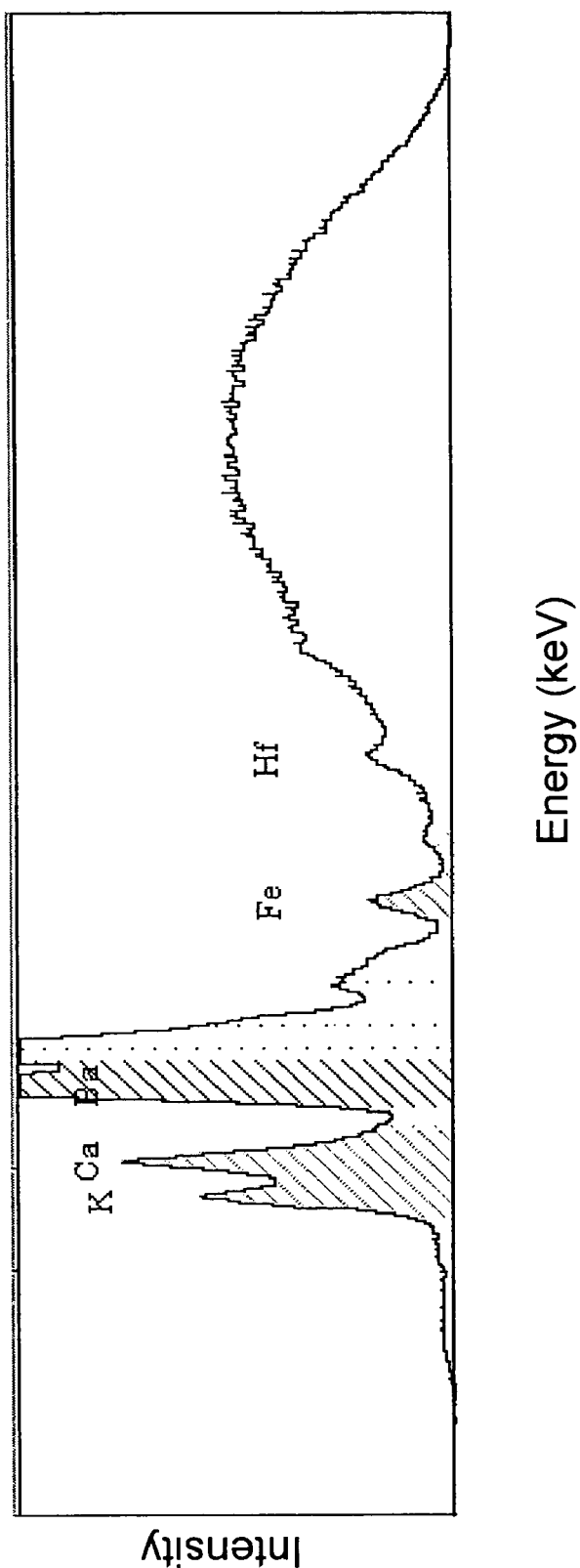
FIG. 3 is a fluorescent X-ray spectrum chart of a sample material.
Figure 4:
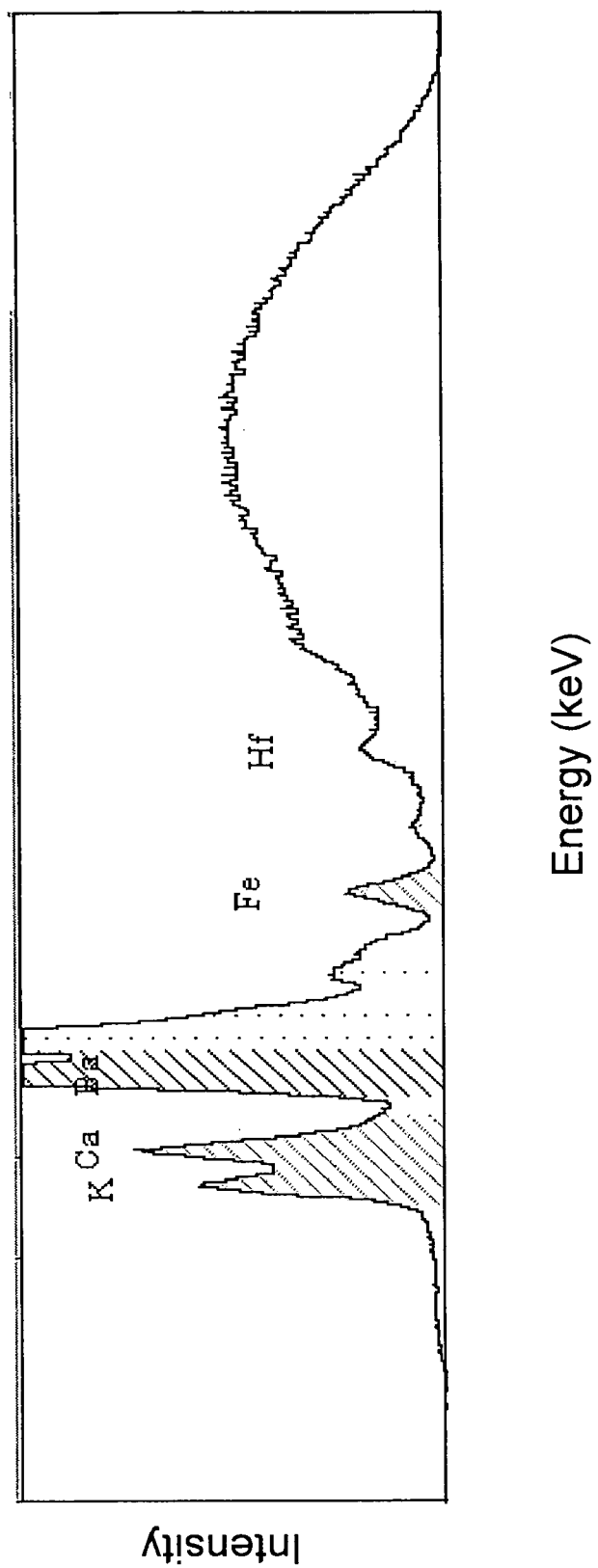
FIG. 4 is a fluorescent X-ray spectrum chart of a reference sample 1.
Figure 5:
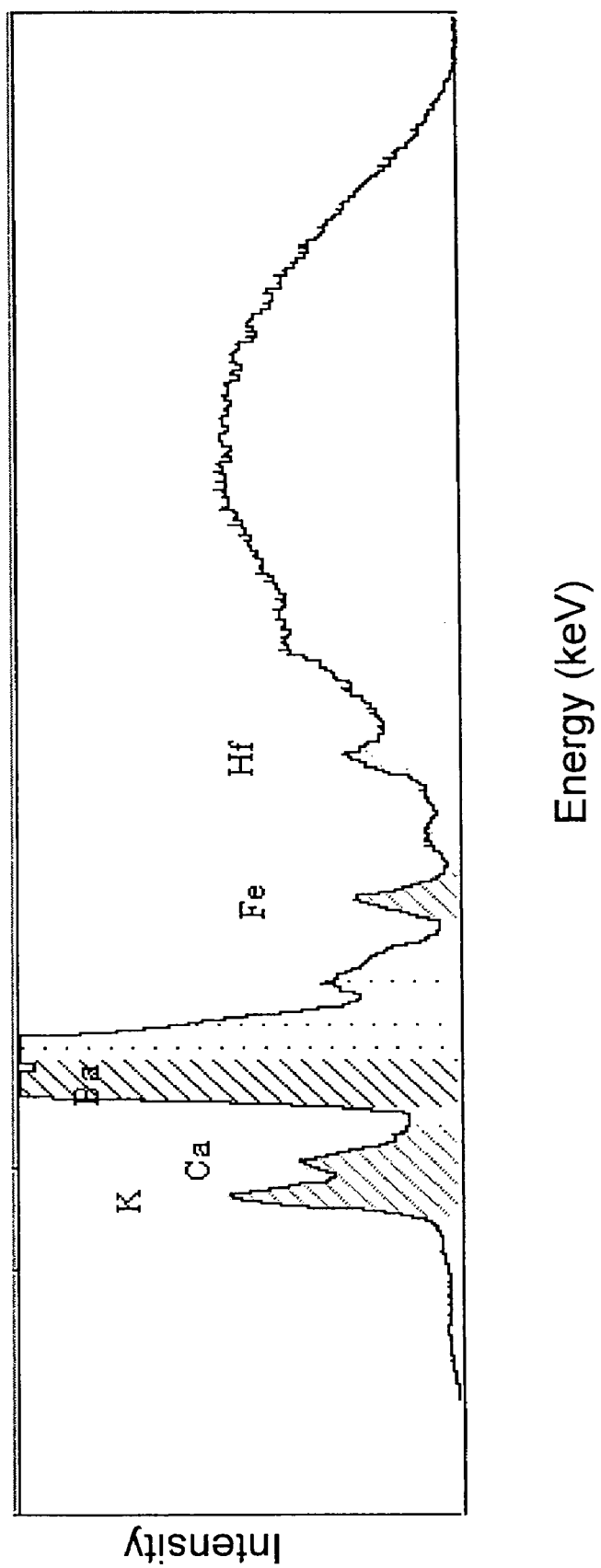
FIG. 5 is a fluorescent X-ray spectrum chart of a reference sample 2.
Figure 6:
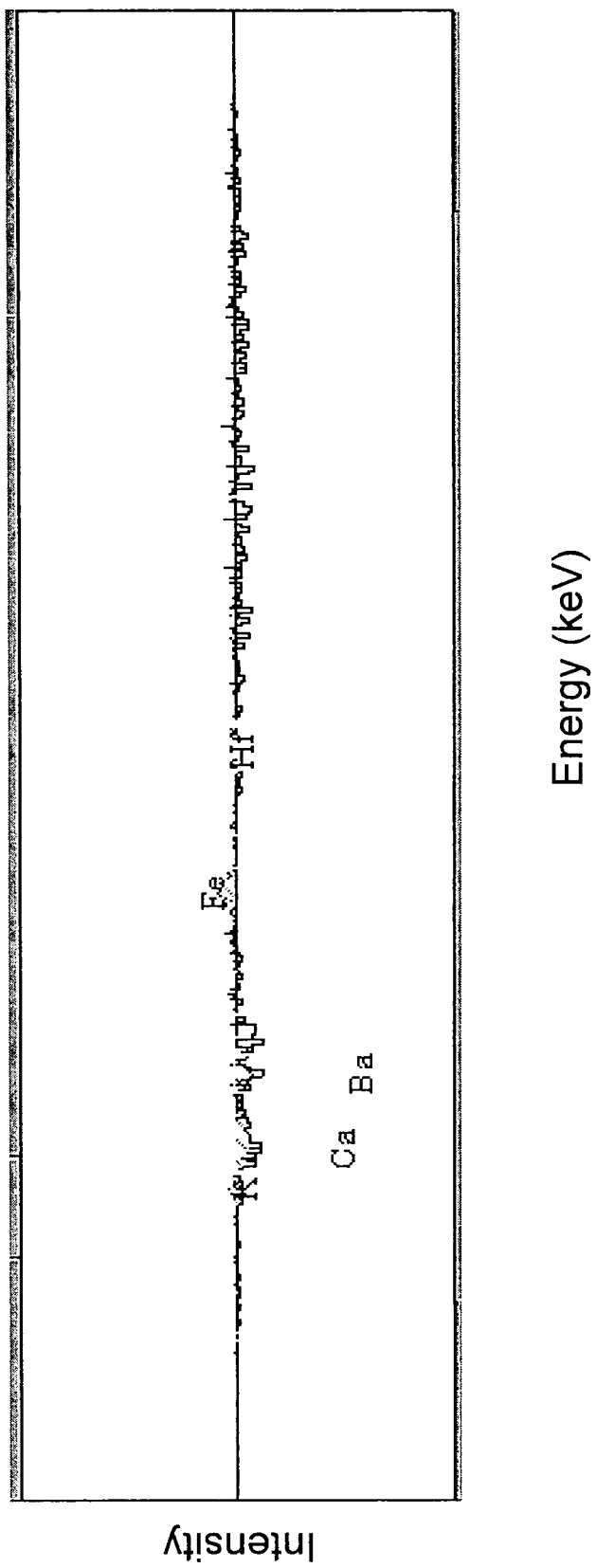
FIG. 6 shows the difference in the fluorescent X-ray spectrum charts between the sample material and the reference sample 1.
Figure 7:
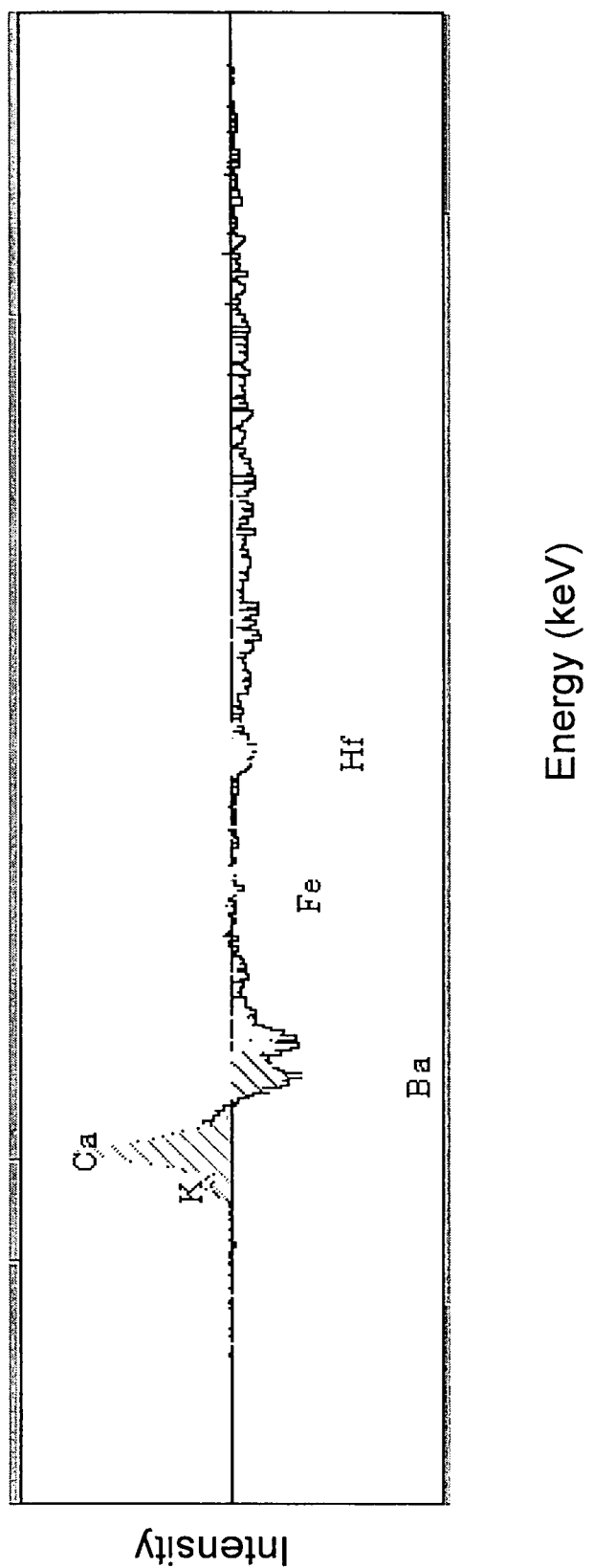
FIG. 7 shows the difference in the fluorescent X-ray spectrum charts between the sample material and the reference sample 2.
Figure 8:
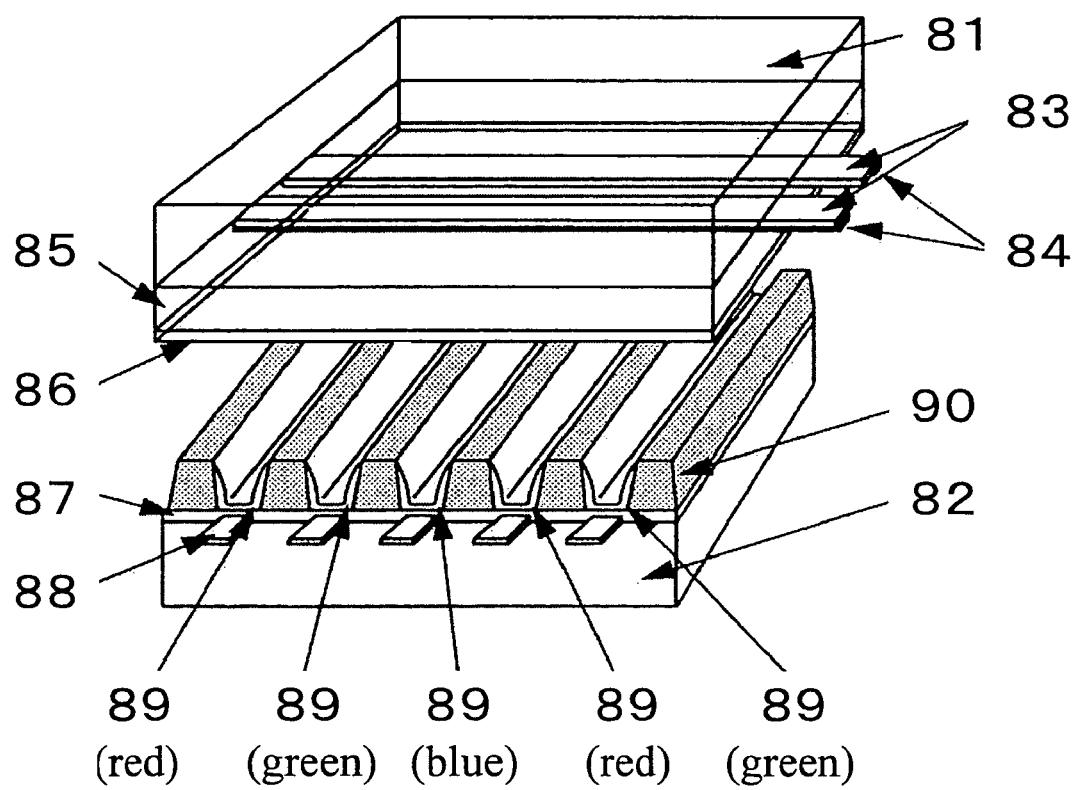
FIG. 8 is a diagram of the structure of a PDP.
Figure 9:
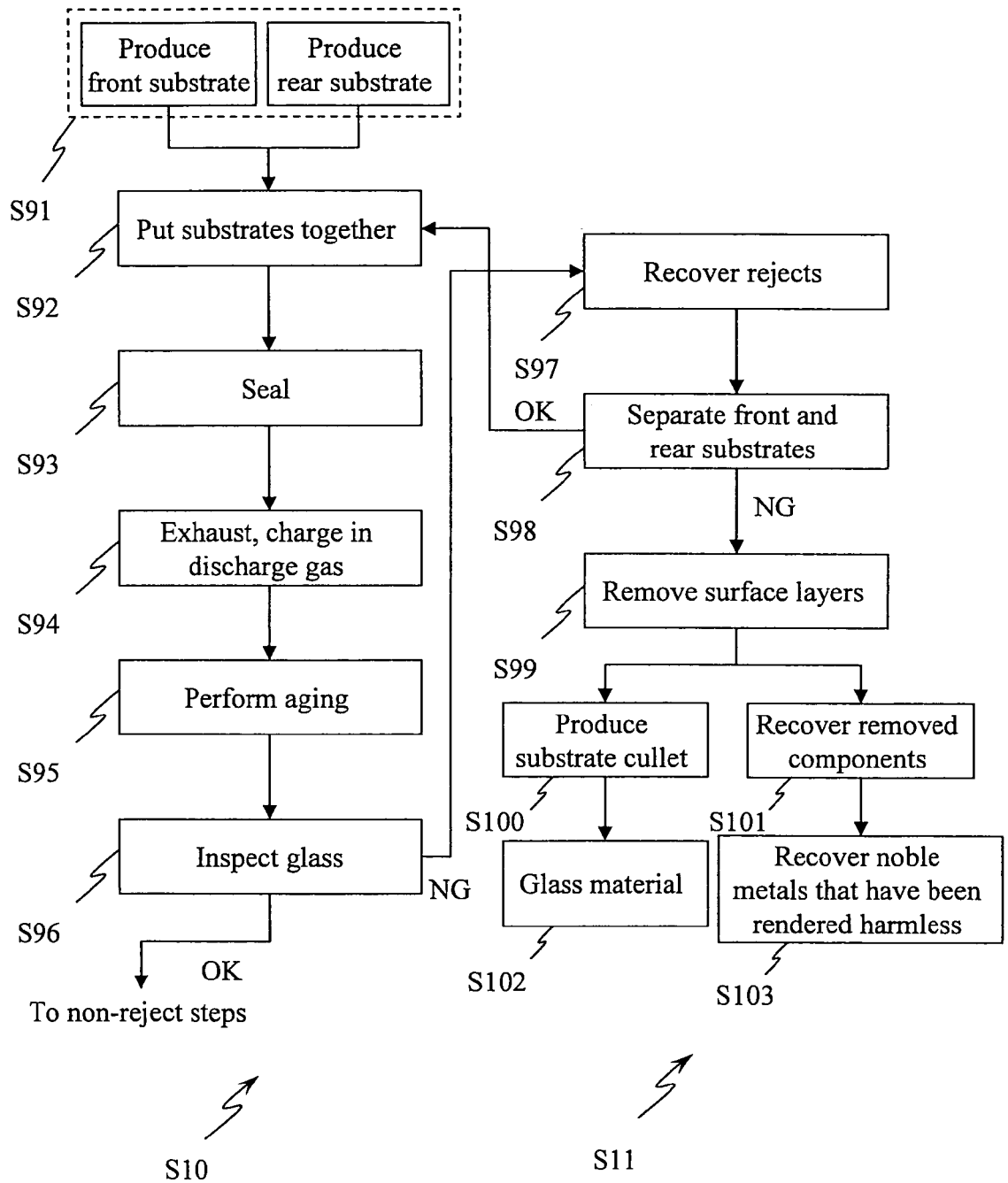
FIG. 9 is a flowchart of a conventional PDP production step and recycling step.

FIG. 3 is a spectrum chart produced by fluorescent X-ray analysis of the sample material. FIGS. 4 and 5 are spectrum charts for the reference samples 1 and 2, measured in the same manner. FIG. 6 shows the difference in the X-ray spectrum charts between the sample material and the reference sample 1, and FIG. 7 shows the difference in the X-ray spectrum charts between the sample material and the reference sample 2. In this case, the sample material can be determined to be the reference sample with fewer variations in the spectrum difference results.

A comparison of FIGS. 6 and 7 reveals that the sample material of this example is sample 1, that is, glass made by Company A.

Other Embodiments (A)

In Example 1, the compositions were analyzed in the glass composition analysis step S19, and substrates with the sample compositions were identified, but it is also possible to identify such substrates by whether or not they contain elements having a characteristic composition, or the amount in which such elements are contained. Because potassium, calcium, iron, strontium, zirconium, barium, hafnium, and other such elements contained in the glass of a substrate have a characteristic signature in their contained amounts, whether or not these elements are contained, or the amounts in which they are contained, may be used.

(B)

Another method is to make use of software that is standard equipment in the fluorescent X-ray analyzer 11 to identify the sample materials in the glass composition analysis step S19. In general, fluorescent X-ray analyzers come with preinstalled software for comparing spectra and evaluating their similarity (called spectrum comparison software, spectrum matching software, or the like). One such type of software measures in advance the compositions of the substrate that will serve as a reference sample, and stores the spectra thereof. Therefore, it is possible to identify between various substrates by using the above-mentioned software to compare the measured spectrum of a recovered substrate with the stored spectra.

For example, a fluorescent X-ray analyzer made by SII comes with a function, called "spectrum matching," that evaluates how well a measured spectrum matches the stored spectra. With spectrum matching, the degree of agreement of the spectra is expressed as a percentage.

Using this function, the spectral waveforms of reference samples 1 and 2 were registered and compared with the spectral waveform of the sample material. As a result, the spectral waveform of the sample material was identified to be the spectrum of sample 1 at an agreement of 99.8%. This result was the same for Examples 1 and 2, and its can be seen that this method is also effective.

(C)

A fluorescent X-ray analyzer was used in the above elements of the present invention, but the method for analyzing the substrates can be any ordinary element analysis method. For instance, inductively coupled plasma mass spectroscopy (ICP-MASS), atomic absorption analysis (AA), or the like may be used instead.

INDUSTRIAL APPLICABILITY

The glass identification method and glass identification apparatus of the present invention can be used in the recycling industry for glass substrates of image display devices. In addition, it can be applied to the recycling of glass products used in furniture and window panes in the construction industry, in glass bottles used in the food industry, and so forth.

The invention claimed is:

1. A glass recovery method for recycling glass of a display panel, comprising:
    separating the display panel into a front glass and a rear glass;
    analyzing a glass composition by using a first side that is included in the front glass or the rear glass and has not undergone a glass processing;
    removing a surface layer of a second side that is included in the front glass or the rear glass and has undergone the glass processing; and
    making the front glass or the rear glass into cullet.

2. The glass recovery method according to claim 1 wherein analyzing the glass composition includes:
    irradiating the first side of the front glass or the rear glass with X-rays to obtain a fluorescent X-ray spectrum for the front glass or the rear glass; and
    identifying the type of glass included in the front glass or the rear glass by analyzing and comparing a fluorescent X-ray spectrum group for a specific glass with the fluorescent X-ray spectrum of the front glass or the rear glass,
    wherein identifying the type of glass involves performing compositional analysis of the fluorescent X-ray spectrum of the front glass or the rear glass compositional analysis of the fluorescent X-ray spectrum group of the specific glass, comparing the analysis results, and determining the degree of agreement.

3. The glass recovery method according to claim 2, wherein the specific glass includes at least one element selected from potassium, calcium, iron, strontium, zirconium, barium, and hafnium.

4. The class recovery method according to claim 1, wherein the display panel is a plasma display panel.

5. The glass recovery method according to claim 4, wherein at least one of the front glass and the rear glass includes at least one element selected from potassium, calcium, iron, strontium, zirconium, barium, and hafnium.

6. The glass recovery method according to claim 5, wherein the specific glass includes at least one element selected from potassium, calcium, iron, strontium, zirconium, barium, and hafnium.

7. The glass recovery method according to claim 1, wherein at least one of the front glass and the rear glass includes at least one element selected from potassium, calcium, iron, strontium, zirconium, barium, and hafnium.

8. The glass recovery method according to claim 7, wherein the specific glass includes at least one element selected from potassium, calcium, iron, strontium, zirconium, barium, and hafnium.

9. The glass recovery method according to claim 1, wherein analyzing the glass composition includes:
    irradiating the first side of the front glass or the rear glass with X-rays to obtain a fluorescent X-ray spectrum for the front glass or the rear glass; and
    identifying the type of glass included in the front glass or the rear glass by analyzing and comparing the fluorescent X-ray spectrum group for a specific glass with the fluorescent X-ray spectrum of the front glass or the rear glass,
    wherein identifying the type of glass involves finding the different between the fluorescent X-ray spectrum of the front glass or the rear glass and the various spectra of the fluorescent X-ray spectrum group of the specific glass, and determining the degree of agreement.

10. The glass recovery method according to claim 9, wherein the specific glass includes at least one element selected from potassium, calcium, iron, strontium, zirconium, barium, and hafnium.

11. The class recovery method according to claim 9, wherein the display panel is a plasma display panel.

12. The glass recovery method according to claim 11, wherein at least one of the front class and the rear class includes at least one element selected from potassium, calcium, iron, strontium, zirconium, barium, and hafnium.

13. The class recovery method according to claim 12, wherein the specific glass includes at least one element selected from potassium, calcium, iron, strontium, zirconium, barium, and hafnium.

14. The glass recovery method according to claim 9, wherein at least one of the front glass and the rear glass includes at least one element selected from potassium, calcium, iron, strontium, zirconium, barium, and hafnium.

15. The glass recovery method according to claim 14, wherein the specific glass includes at least one element selected from potassium, calcium, iron, strontium, zirconium, barium, and hafnium.

16. The glass recovery method according to claim 1, wherein the display panel is a plasma display panel.

17. The glass recovery method according to claim 1, wherein at least one of the front glass and the rear glass includes at least one element selected from potassium, calcium, iron, strontium, zirconium, barium, and hafnium.

* * * * *